United States Patent [19]

Wieder et al.

[11] 4,000,561
[45] Jan. 4, 1977

[54] DEVICE FOR SEVERING TUBULAR MEMBERS

[76] Inventors: Horst K. Wieder, 1207 Riverview Lane, Watertown, Wis. 53094; Klaus A. Wieder, Rte. No. 1, Helenville, Wis. 53137

[22] Filed: July 14, 1975

[21] Appl. No.: 595,719

[52] U.S. Cl. .................................. 30/124; 30/241
[51] Int. Cl.² ............................................ B26B 13/22
[58] Field of Search ............ 30/124, 182, 241, 113; 83/580, 588, 636

[56] References Cited
UNITED STATES PATENTS

| | | | |
|---|---|---|---|
| 1,066,365 | 7/1913 | Battin | 30/113 |
| 1,119,220 | 12/1914 | Bates | 30/113 |

Primary Examiner—James L. Jones, Jr.
Assistant Examiner—J. C. Peters
Attorney, Agent, or Firm—John M. Diehl

[57] ABSTRACT

Hand operated device for transversely severing polymeric synthetic resinous tubular members comprises resilient plastic housing members which snap together and a finger operated sliding member which carries a portion of a razor blade mounted in a described manner.

7 Claims, 28 Drawing Figures

DEVICE FOR SEVERING TUBULAR MEMBERS

CROSS-REFERENCES

The device of the invention is particularly adapted for severing tubular members described in my co-pending application Ser. No. 489,169 filed July 17, 1974, now U.S. Pat. No. 3,877,430, entitled "Artificial Insemination Apparatus".

FIELD

This invention relates to a cutting device and more particularly to a hand operated device for transversely severing polymeric synthetic resinous tubular members.

PRIOR ART

No device having similar or comparable features, attributes and characteristics is known to have been heretofore described.

SUMMARY

Cutting devices such as scissors or a hand held razor blade or pocket knife may be used to transversely sever a thin-walled plastic (polymeric synthetic resinous) tube but by using such devices it is not normally possible to obtain a cut which is accurately normal (perpendicular) to the axis of the tube or which is clean and devoid of burs.

For the purpose of providing a severed artificial insemmination tube (straw) for use in the apparatus described in the aforementioned application Ser. No. 489,169 filed July 17, 1974, it is desirable and may be necessary to provide a very clean and very accurately made cut which is substantially precisely normal or perpendicular to the axis of the tube and for this purpose no hand-held hand-operated simple device is known which can be utilized to accomplish the desired objective.

It is also desirable to provide such a device which can be made relatively inexpensively and which is very simple to assemble and disassemble in order to facilitate cleaning or sterilization as may be needed and which will operate reliably under adverse conditions.

As examples of such adverse conditions: the device may be carried in the user's pocket; it may be thrown onto the floor of a vehicle repeatedly; it may be carried over rough roads while bouncing on the floor of a vehicle or in a suitable container such as a tool box, valise, veterinarian's bag or the like without any protection whatever; it may be left out in inclement weather such as snow, rain or sleet or bright sunlight. It must be possible to readily disassemble, clean and re-assemble the device after it has undergone such treatment.

Accordingly, the device provided comprises two simple resilient plastic (polymeric synthetic resinous) members which in preferred embodiments may be placed in contact with each other in a pre-selected position and then caused to engage by simple rotational movement which causes the resilient members to be slightly deflected and interlocked; in other words, the two housing members may be "snapped" together. Simply by reversal of these movements the two members can be disassembled from each other. Received internally with respect to the two housing members there is provided a simple plastic sliding member which is disposed between the two members during assembly. The only other two parts in the device are a spring to bias the sliding member and a blade carried by the sliding member. The angles at which the blade is mounted are critical as described below.

A notable feature of the device is that it comprises only three plastic members and each of the three members is adapted to be made with a two-part mold comprising on cams, slides or the like and thus the three parts may be made economically in a family die and the entire device may be assembled with an absolute minimum of labor.

OBJECTS

It is therefore an object of the invention to provide an improved device for severing plastic tubes.

Another object is such a device which may be made economically.

Another object is such a device which may be hand held and hand operated.

Another object is such a device which may be readily disassembled, cleaned and assembled under adverse conditions.

Another object is such a device which will withstand adverse conditions of use, transport and storage.

Further objects will become apparent from the drawings and descriptions which follow.

DRAWINGS

In the drawings like reference numerals refer to like parts and:

Figure 3:
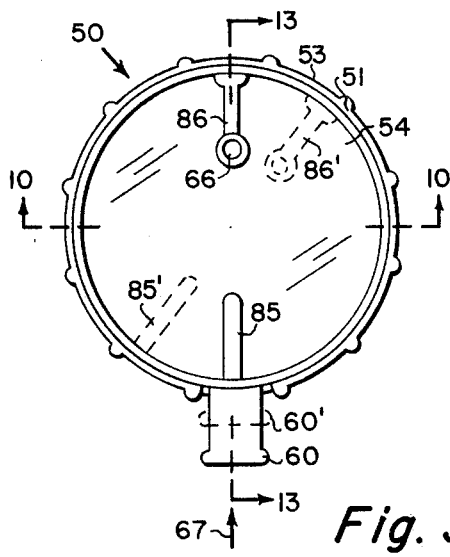
FIG. 3 is a top plan view of a preferred embodiment in accordance with the invention.
Figure 4:
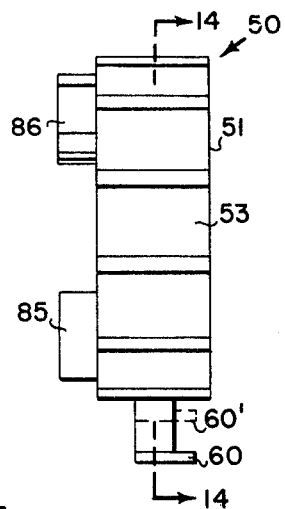
FIG. 4 is a side elevation of the embodiment of FIG. 3.
Figure 5:
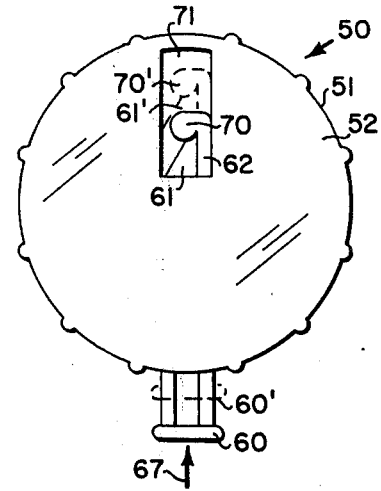
FIG. 5 is a bottom plan view of the embodiment of FIGS. 3 and 4.
Figure 6:
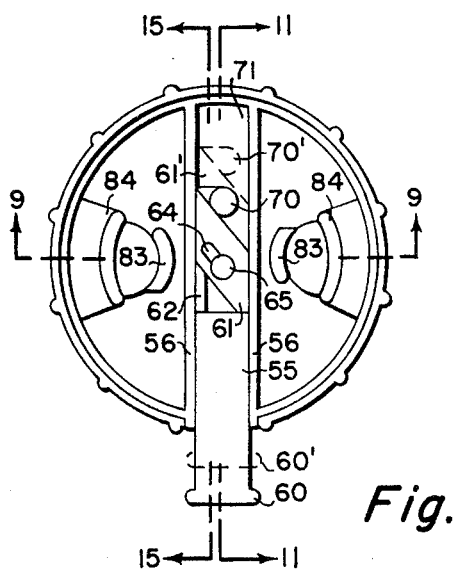
FIG. 6 is a top plan view of the embodiment of FIGS. 3 to 5 with its top housing member removed.
Figure 7:
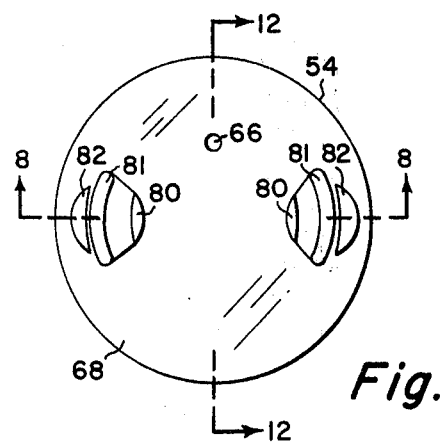
FIG. 7 is a bottom plan view of the top housing member of the embodiment of FIGS. 3 to 5 which is removed in the view of FIG. 6.
Figure 8:
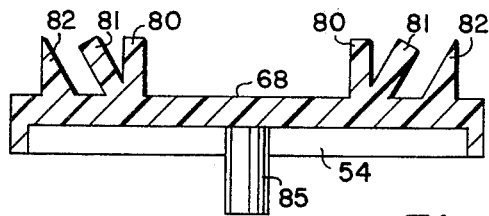
FIG. 8 is a cross-sectional view taken on lines 8—8 in FIG. 7.
Figure 9:
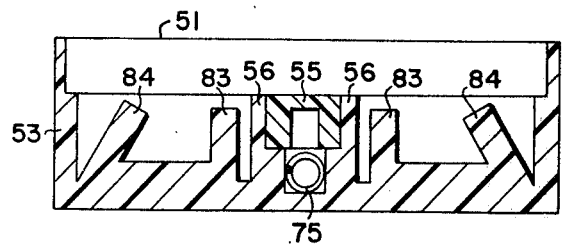
FIG. 9 is a cross-sectional view taken on lines 9—9 in FIG. 6.
Figure 10:
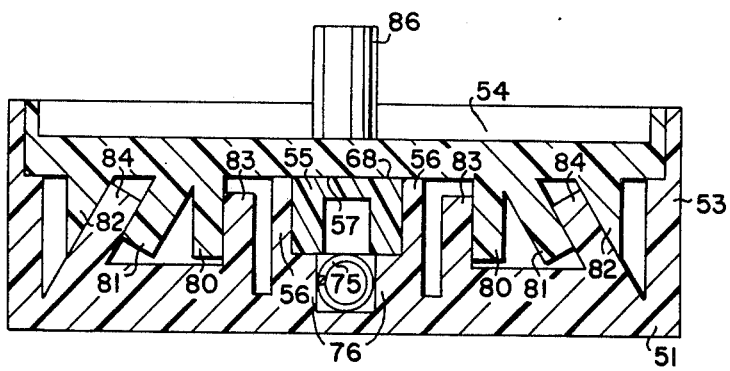
Figure 11:
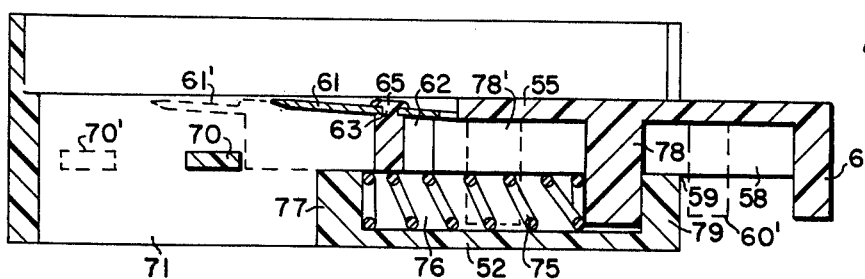
Figure 12:
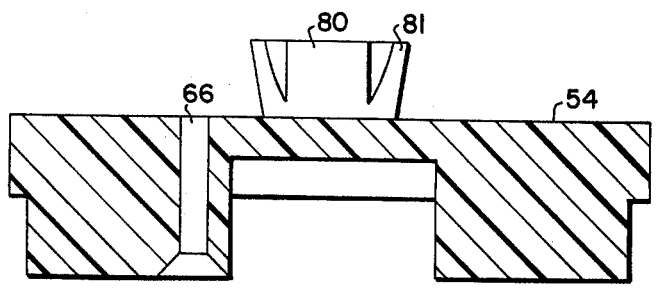
Figure 13:
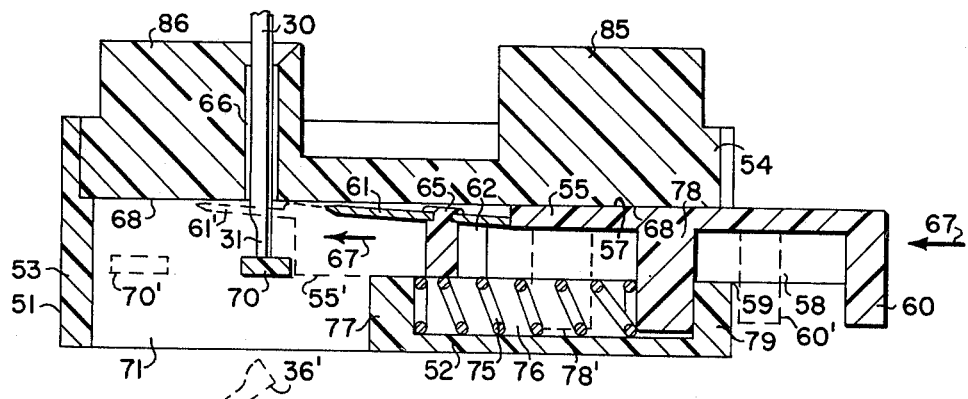
Figure 14:
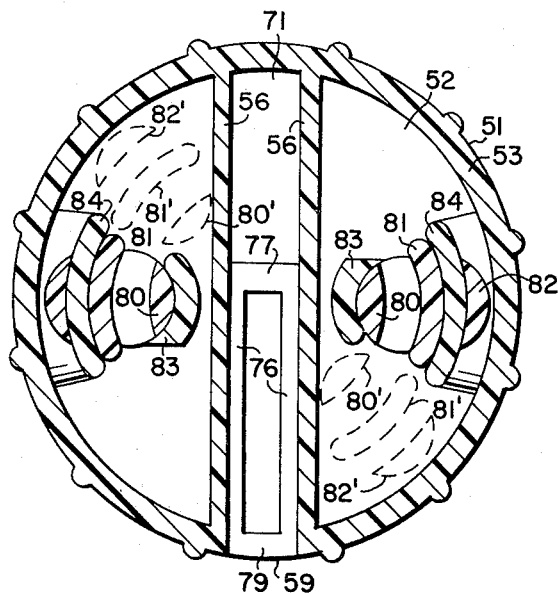
Figure 15:
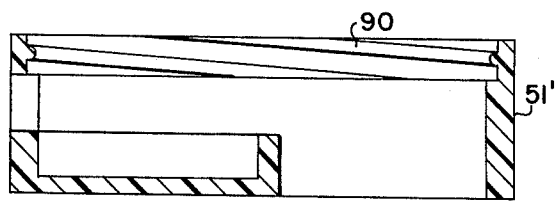
Figure 16:
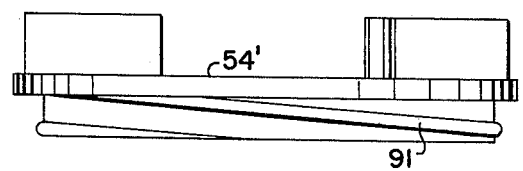
Figure 17:
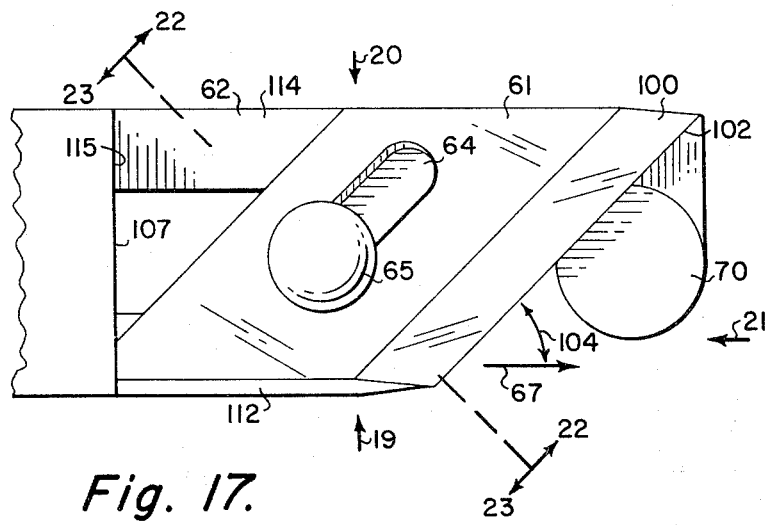
Figure 18:
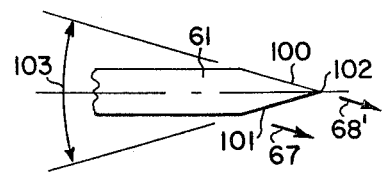
Figure 19:
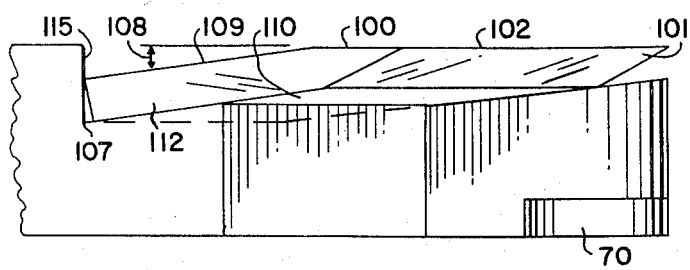
Figure 20:
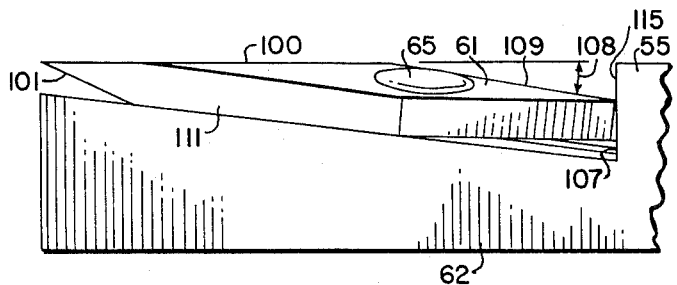
Figure 21:
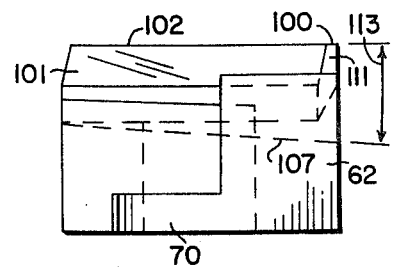
Figure 22:
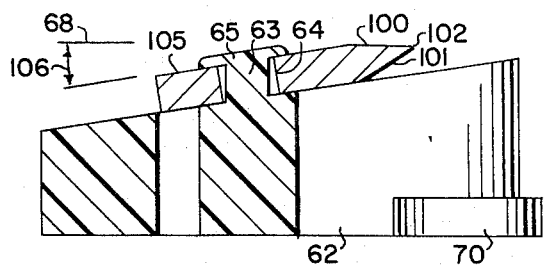
Figure 23:
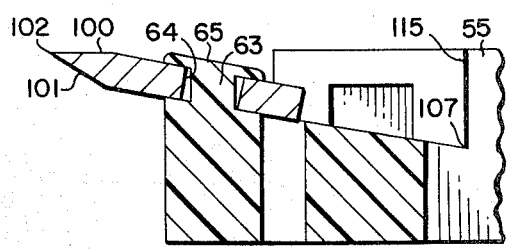
Figure 24:
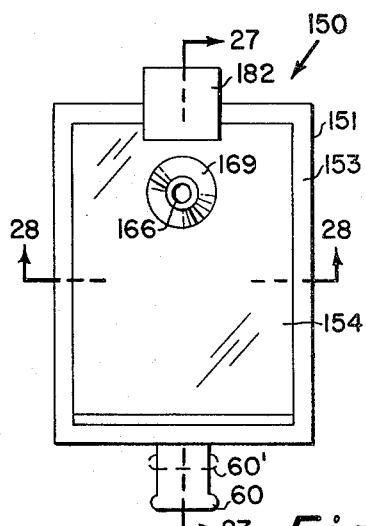
Figure 25:
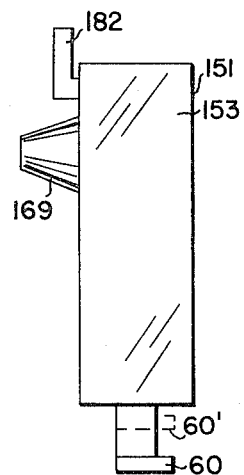
Figure 26:
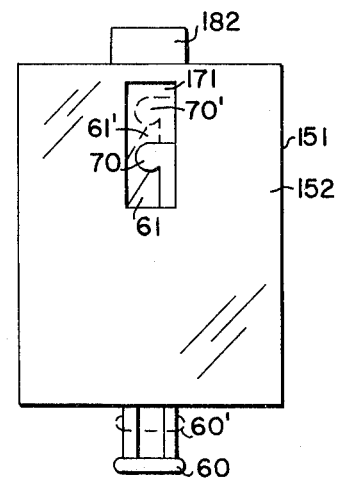
Figure 27:
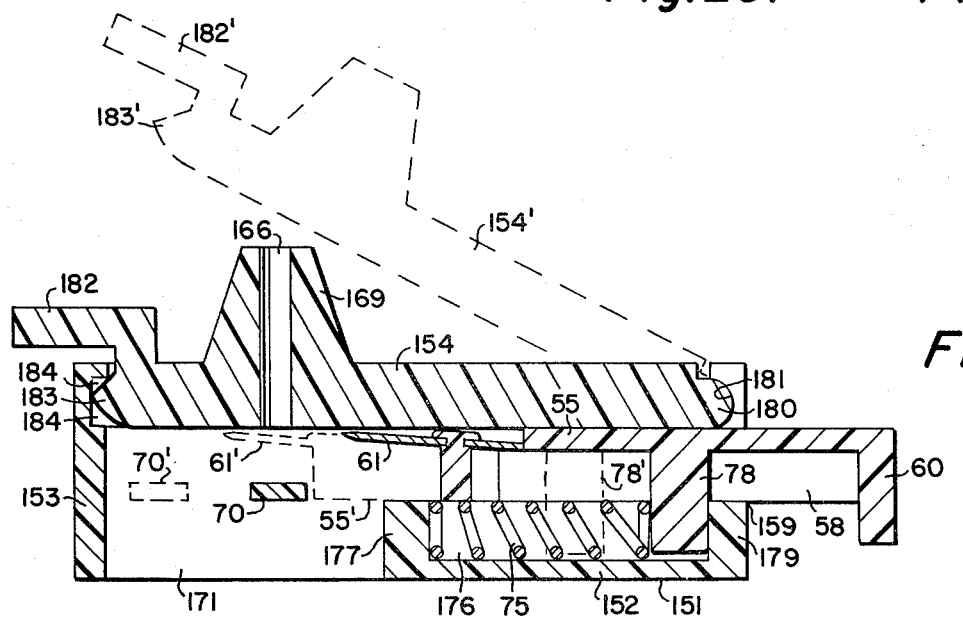

FIG. 10 is a cross-sectional view taken on lines 10—10 in FIG. 3 which includes cross-sectional views corresponding to those of FIGS. 8 and 9 taken respectively on lines 8—8 in FIG. 7 and 9—9 in FIG. 6;

FIG. 11 is a cross-sectional view taken on lines 11—11 in FIG. 6;

FIG. 12 is a cross-sectional view taken on lines 12—12 in FIG. 7;

FIG. 13 is a cross-sectional view taken on lines 13—13 in FIG. 3 which includes cross-sectional views corresponding to those of FIGS. 11 and 12 taken respectively on lines 11—11 in FIG. 6 and 12—12 in FIG. 7;

FIG. 14 is a cross-sectional view taken on lines 14—14 in FIG. 4 with members 55 and 75 removed;

FIG. 15 is a cross-sectional view of a modification of member 51 of FIGS. 3–14 which corresponds to a view which would have been taken of such embodiment on lines 11—11 in FIG. 6;

FIG. 16 is a side elevation from the aspect of FIG. 4 of a modification of the embodiment of member 54 of FIGS. 7, 8 and 12 which is adapted to cooperate with the embodiment of FIG. 15 to provide an assembled modification of the device of the embodiment of FIGS. 3–14;

FIG. 17 is a fragmentary top plan view of a cutting portion of the device corresponding to an enlarged fragmentary view of a portion of FIG. 6;

FIG. 18 is a fragmentary end elevation of member 61 of FIG. 17;

FIG. 19 is a side elevation of the embodiment of FIG. 17 taken from the aspect of arrow 19 in FIG. 17;

FIG. 20 is a side elevation of the embodiment of FIG. 17 taken from the aspect of arrow 20 in FIG. 17;

FIG. 21 is an end elevation of the embodiment of FIG. 17 taken from the aspect of arrow 21 in FIG. 17;

FIG. 22 is a cross-sectional view taken on lines 22—22 in FIG. 17;

FIG. 23 is a cross-sectional view taken on lines 23—23 in FIG. 17;

FIG. 24 is a top plan view of a modification of the embodiment of FIGS. 3–14 and 17–23 corresponding to the view of FIG. 3;

FIG. 25 is a side elevation of the modified embodiment of FIG. 24 corresponding to the view of FIG. 4;

FIG. 26 is a bottom plan view of the embodiment of FIGS. 24 and 25 corresponding to the view of FIG. 5;

FIG. 27 is a cross-sectional view taken on lines 27—27 in FIG. 24; and

Figure 28:
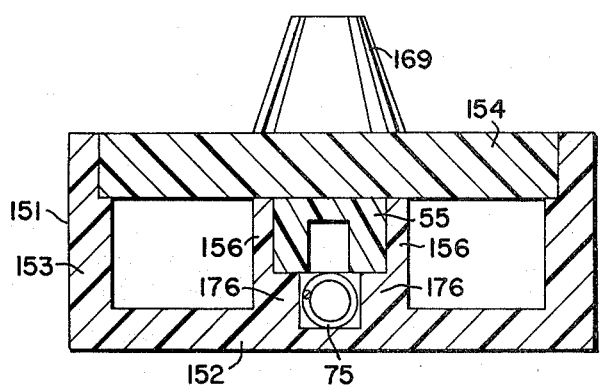

FIG. 28 is a cross-sectional view taken on lines 28—28 in FIG. 24.

DESCRIPTION

Figure 1:
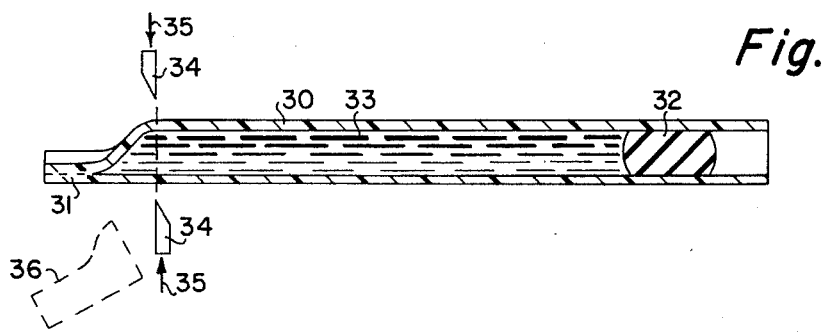
FIG. 1 is a cross-sectional view of a tubular member to be severed by the device of the invention.
Figure 2:
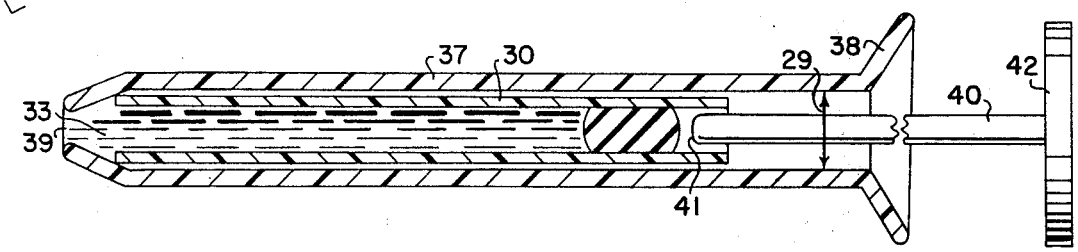
FIG. 2 is a cross-sectional view showing a step in the utilization of the device of FIG. 1 after being severed, as by the device of the invention.

FIGS. 1 and 2 correspond to FIGS. 4 and 5 in copending application Ser. No. 489,169 filed July 17, 1974, for "Artificial Insemination Apparatus". In FIG. 1 there is shown an artificial insemination straw comprising plastic tubular member 30, that is, a tubular member made from polymeric synthetic resinous material, which is sealed at one end as indicated at 31 and has received in its other end elastomeric piston member 32. Contained within tube 30 between sealed end 31 and piston 32 there may be provided liquid 33 for artificial insemination of an animal.

To accomplish such insemination, tube 30 is severed near end 31 as indicated schematically by blades 34 traveling as indicated by arrows 35. When tubular member 30 is thus severed, the end which is heat sealed at 31 drops away as indicated in dashed lines at 36 and the thus severed member 30 containing liquid 33 and piston 32 may be received in a sheath tube 37 which may have an inside diameter indicated at 29 which is larger than the outside diameter of tube 30. Sheath tube 37 may be provided with an outwardly extending or protruding portion or flange 38 at one end and with a converging portion to provide a terminal orifice 39 at the other end. Push rod or pusher member 40 which may have a convex end at 41 and a widened portion or head at 42 may then be inserted in sheath tube 37 and in a straw 30 so that end 41 is adjacent piston member 32. By exerting finger pressure on portion 42, rod 40 may be operated to drive piston 32 to expel liquid 33 through orifice 39.

Referring now to FIGS. 3–14 there may be provided in accordance with the invention a device which may be particularly suited for accomplishing the severing of tubular member 30 indicated schematically by blades 34 and arrows 35 in FIG. 1. The device is indicated generally at 50 and may comprise a first housing member 51 having a bottom 52 and side walls 53 and a second housing member 54 which may be attached to housing member 51 in the manner hereinafter described.

Sliding member 55 may be slidably received between interior walls 56 of member 51 and may be held in place by upper housing member 54 slidably acting abuttably against the upper surface of member 55 as indicated at 57.

Sliding member 55 may be provided with a handle portion 58 which may extend through aperture 59 in side wall 53 and terminate in portion 60 adapted to be contacted by an operator's finger or thumb. At the opposite end of sliding member 55 from handle portion 58 a cutting blade 61 may be attached to portion 62 of sliding member 55 in any suitable manner such as by heating and upsetting an upwardly extending thermoplastic projection 63 which extends upwardly through aperture 64 in blade 61 as shown at 65 (see especially FIGS. 6, 17, 20, 22 and 23). Tubular aperture 66 may be provided in member 54 to receive and retain a tube such as tube 30 in the path of blade 61, with the axis of the tube normal to the direction of travel of sliding member 55 and blade 61 which is indicated by arrow 67.

Laterally extending from portion 62 of sliding member 55 there may be provided a guide portion 70 against which sealed end 31 of tube 30 may abut (FIG. 13) prior to being cut, to retain tube 30 in such relation to blade 61 that tube 30 is severed the proper distance from end 31 when sliding member 55 is operated in the direction shown by arrows 67 to occupy the position shown in dashed lines at 60', 55' and 61' whereupon guide portion 70 occupies the position shown in dashed lines at 70' and the severed end of tube 30 may fall free as indicated at 36', guide portion 70 having been removed from its position abutting end 31 to the position shown in dashed lines at 70'.

Compression spring 75 may be received in member 51 between lower portions 76 of walls 56 with one of its ends abutting transverse wall 77 which extends between walls 76 and its other end abutting downwardly extending portion 78 of sliding member 55 which in turn may abut a portion 79 of wall 53 immediately below aperture 59 to prevent member 55 from being biased by spring 75 to a position entirely removed from the device.

Thus when sliding member 55 is slidingly operated in the direction shown by arrow 67 to cause blade 61 to sever a tube 30, downwardly extending portion 78 acts against spring 75 and compresses spring 75 and approaches closer to wall 77 as indicated at 78' in dashed lines.

As soon as pressure is removed on portion 60 then spring 75 acts against portion 78 to cause member 55 to return to its original position shown in full lines.

Housing members 51 and 54 may be attached together by interlocking, deformable members of thermoplastic material. By making members 51 and 54 of deformable thermoplastic polymeric resinous material such as ABS, high impact polystyrene, polypropylene or the like there may be provided integrally molded extending interlocking deformable members to attach members 51 and 54 together. Thus, member 54 may be provided at each of two places on opposite sides with an inner downwardly extending member 80, a middle slantwardly downwardly extending member 81 and an outer downwardly extending member 82 and member 51 may be provided interiorly at each of two corresponding locations with deformable members extending upwardly from the interior surface of bottom 52. At each location these may comprise an inner member 83 extending substantially directly upwardly and an outer member 84 extending slantwardly upwardly.

Member 54 may be provided with two upwardly extending grip portions 85 and 86 one of which, 86, may have aperture 66 provided therein.

To assemble the device, after first placing spring 75 and sliding member 55 in lower housing member 51, top housing member 54 may be placed on member 51 in a position rotated with respect to its final position as indicated in dashed lines by the positions of parts 80, 81, 82, 85 and 86 indicated at 80', 81', 82', 85' and 86' in FIGS. 3 and 14. By action of the fingers, member 54 may be rotated with respect to member 51 to cause members 84 and 81 in particular to be slightly deformed so that parts 80, 81, 82, 83, 84, 85 and 86 then occupy the positions shown in full lines particularly in FIGS. 3, 10 and 14.

Rather than providing members such as member 80, 81 82, 83 and 84 to attach members 51 and 54 together, they may be attached by other means. For example, member 51 may be provided with internal threads 90 as indicated for member 51' in FIG. 15 and member 54 may be provided with external threads 91 as indicated for member 54' in FIG. 16. Members 51 and 54 may then be attached together by threaded engagement of threads 90 and 91.

Referring now to FIGS. 17–23, blade 61 is preferably provided as a portion of a common razor blade which is V-ground to provide two V-ground surfaces 100 and 101 which meet at cutting edge 102. Ground surfaces 100 and 101 are distinguished from flat parallel surfaces 105 and 110 which are referred to as "unground" for purposes of distinguishing but may in fact be finished by grinding. Surfaces 100 and 101 may have an angle with respect to each other of on the order of 22° as indicated at 103 but such angle may be from 18° to 32°.

It is critical to the invention that surface 100 which is planar (and therefore lies in a plane) travels in the plane in which it lies during the cutting operation and that said plane is both normal to the axis of the tube to be cut and more important is parallel to the surface 68 of member 54 (FIG. 13) (indicated in FIG. 18 as 68') which abuts sliding member 55 and is parallel to the direction of movement of sliding member 55 which is indicated by arrow 67. It is also necessary that edge 102 be at an angle with respect to direction 67 as indicated at 104. Accordingly, blade 61 is preferably so disposed that its upper unground surface indicated as 105 is at an angle indicated as 106 (FIG. 22) to the plane of surface 68. Also, the corner 109 at which surfaces 105 and 112 join is at angle 108 to the plane of surfaces 102 and 68 (FIGS. 19 and 20). Finally, internal corner 107 of portion 62 of member 55, corner 107 being defined by the intersection of supporting surfaces 114 of member 55 (against which lower unground surface 110 of blade 61 lies) and transverse verticle surface 115 of member 55, is at angle 113 to the plane of surface 102 (FIG. 21) and thus the unground surfaces 105 and 110 are at an angle (angle 113) to each and any plane which is transverse to direction 67.

Referring now to FIGS. 24–29 it may be seen that a device in accordance with the invention may be rectangular in plan (FIGS. 24 and 26) rather than circular in plan and the principal parts may be attached together by means other than shown for previously described embodiments.

Thus lower housing member 151 is generally rectangular in shape and comprises bottom 152 and side walls 153 and upper housing member 154 is generally rectangular in shape and is provided with a boss 169 which is provided with a hole or aperture 166 in which a straw comprising a tube such as tube 30 may be inserted to thereby retain tube 130 in the desired position with its axis normal to the direction of travel of sliding member 55 as indicated by arrows 67. Sliding member 55 which may be identical with that shown for previous embodiments may be received in portions of lower housing member 151 which may be similar to or identical to those hereinbefore described in conjunction with member 51. Thus sliding member 55 may be received between walls 156 of member 151. Underlying walls 156 there may be provided walls 176 to receive spring 75 which may abut at one end against wall 177 extending between walls 176 and abut at the other end against portion 78 extending downwardly from sliding member 55. Portion 78 may be received against wall 179 provided as a portion of one of side walls 153 immediately below aperture 159 which receives handle portion 58 of sliding member 55. Aperture 171 provided in member 153 may be similar in form and serve an identical purpose to aperture 71 in the embodiments previously described, said purpose being to allow room for the severed portion of the tube of fall out of the device.

Member 154 may be provided with rounded portion 180 at one edge which may be received in concavedly rounded portion or channel 181 parallel to and adjacent to the upper edge of one of walls 153 in member 151. Channel 184 may be provided parallel to and adjacent to the upper edge of an opposite one of walls 153 in member 151 and member 154 may be provided with an edge 183 adapted to deform the upper edge 189 of wall 153 immediately above channel 184. Such deformation may take place both as member 154 is snapped into place to occupy the position shown in full lines in FIG. 27 and as it is pulled upward to cause it to hinge upwardly into a position such as that indicated in dashed lines at 154', 183' and 182'. It may be pulled upward by utilizing tab 182 extending therefrom. When thus pulled upward, the upper surface of edge 183 may deform upper edge 189 of wall 153 above channel 184 to make possible its release and when it is closed, edge 189 may be deformed by the lower surface of edge 133 so that it snaps in place, being retained in the closed position by edge 189 (after it resiliently returns to the position shown in full lines) acting against the upper surface of edge 183.

Thus it may be seen from comparison of the embodiments described above that the general exterior shape of the device of the invention is not critical.

Furthermore, it may be seen that whereas it is preferable to provide means for locking the two principal housing members of the device together by providing these members of a somewhat deformable resilient plastic (polymeric synthetic resinous) material and causing respective interlocking portions of two principal housing members to be deformed or at least one of them to be deformed by suitably applied pressure to disengage said interlocking members and likewise to cause one or both of said interlocking portions respectively on said two housing members to be slightly deformed resiliently to cause said interlocking portions to be engaged. Whereas in the embodiments of FIGS. 3–17 on the one hand and 24–28 on the other hand, the two principal housing members are attached by interlocking of resilient deformable members, they may, of course, be attached by other means such as, for example, by threadedly engaging portions as described in connection with FIGS. 18 and 19.

The interlocking means shown in FIGS. 3–17 for attaching members 51 and 54 together is generally preferable for the reason that each of these members may be made with two part dies, that is, with a punch and die each of which is devoid of cams. Each of parts 54 and 51, after being molded may be withdrawn from the mold by deformation of the deformable parts 80, 81, 82, 83 and 84. Sliding member 55 may also be made in a two part die and thus all the plastic members for this embodiment may be made economically in one family die, devoid of cams, slides and other such extra and costly features.

It will be apparent to those skilled in the art that equivalents may be utilized.

Accordingly, the present invention may be embodied in other specific forms without departing from the spirit or essential attributes thereof and accordingly, reference should be made to the appended claims rather than to the foregoing specification as indicating the scope of the invention.

It is claimed:

1. In a device for transversely severing a polymeric synthetic resinous artificial insemination tube,
a first housing member having a bottom and side walls,
an elongated slide member having two ends,
a second housing member,
a spring, and
a cutting blade,
said slide member:
  slidably received in a portion of said first housing member, and
  having at one of its ends a handle portion which extends outside said first housing member, and
  having said blade attached to it at its other end,
said first housing member:
  having means for attaching it to said second housing member, and
  having means to slidably receive said slide member, and
  having an aperture in a sidewall to receive said handle portion of said slide member, and
  having abutting means to abut a portion of said slide member adjacent to said handle portion to prevent sliding removal of said slide member through said sidewall, and
  having means to receive said spring,
said spring disposed in said first housing member to bias said slide member against said abutting means,
said second housing member:
  having means to attach it to said first housing member, and
  abuttable to a surface of said slide member to retain said slide member in said portion of said first housing member in which it is slidably received, and
  having an aperture to guide a tube to be severed into the path of said blade,
wherein said first and second housing members are attached by resiliently deformable interlocking portions of said attaching means which are provided as part of one of said housing members being interlocked with corresponding interlocking portions provided as attaching means as part of the other of said housing members.

2. In a device for transversely severing a polymeric synthetic resinous artificial insemination tube,
a first housing member having a bottom and side walls,
an elongated slide member having two ends,
a second housing member,
a spring, and
a cutting blade,
said slide member:
  slidably received in a portion of said first housing member, and
  having at one of its ends a handle portion which extends outside said first housing member, and
  having said blade attached to it at its other end,
said first housing member:
  having means for attaching it to said second housing member, and
  having means to slidably receive said slide member, and
  having an aperture in a sidewall to receive said handle portion of said slide member, and
  having abutting means to abut a portion of said slide member adjacent to said handle portion to prevent sliding removal of said slide member through said sidewall, and
  having means to receive said spring,
said spring disposed in said first housing member to bias said slide member against said abutting means,
said second housing member:
  having means to attach it to said first housing member, and
  abuttable to a surface of said slide member to retain said slide member in said portion of said first housing member in which it is slidably received, and
  having an aperture to guide a tube to be severed into the path of said blade,
characterized by the direction of sliding travel of said slide member being normal to the axis of said tube to be severed and by said blade:
  being a portion of a razor blade and being V-ground, and
  being attached to said slide member with its cutting edge at an angle to the direction of travel of said slide member, and
  being attached to said slide member with its unground surfaces at an angle to the upper sliding surface of said slide member, and
  being attached to said slide member with its unground surfaces at an angle to a plane transverse to the direction of travel of said sliding member, and
  being attached at such angles that the plane of one of said V-ground surfaces is parallel to the direction of sliding travel of said slide member and normal to the axis of said tube to be severed.

3. The device of claim 2 wherein said first and second housing members are attached by resiliently deformable interlocking portions of said attaching means which are provided as part of one of said housing members being interlocked with corresponding interlocking portions provided as attaching means as part of the other of said housing members.

4. In a device for transversely severing a polymeric synthetic resinous artificial insemination tube,
a first housing member having a bottom and side walls,
an elongated slide member having two ends,
a second housing member,
a spring, and
a cutting blade,
said slide member:
  slidably received in a portion of said first housing member, and
  having at one of its ends a handle portion which extends outside said first housing member, and
  having said blade attached to it at its other end,
said first housing member:
  having means for attaching it to said second housing member, and
  having to slidably receive said slide member, and
  having an aperture in a sidewall to receive said handle portion of said slide member, and
  having abutting means to abut a portion of said slide member adjacent to said handle portion to prevent sliding removal of said slide member through said sidewall, and
  having means to receive said spring,
said spring disposed in said first housing member to bias said slide member against said abutting means,
said second housing member:
  having means to attach it to said first housing member, and
  abuttable to a surface of said slide member to retain said slide member in said portion of said first housing member in which it is slidably received, and
  having an aperture to guide a tube to be severed into the path of said blade,
characterized by the direction of sliding travel of said slide member being normal to the axis of said tube to be severed and by said blade:
  being a portion of a razor blade and being V-ground, and
  being attached to said slide member at an angle to each of three directions,
    the first of said directions being the direction of sliding travel of said slide member,
    the second of said directions being the direction which is normal to said direction of travel and parallel to the axis of the tube to be severed,
    the third of said directions being the direction which is normal to both said first and said second directions, and
  being attached at such angles that the plane of one of said V-ground surfaces is parallel to the direction of sliding travel of said slide member and normal to the axis of said tube to be severed.

5. The device of claim 4 wherein said first and second housing members are attached by resiliently deformable interlocking portions of said attaching means which are provided as part of one of said housing members being interlocked with corresponding interlocking portions provided as attaching means as part of the other of said housing members.

6. In a device for transversely severing a polymeric synthetic resinous artificial insemination tube,
a housing,
an elongated slide member having two ends,
resilient means to bias said slide member, and
a cutting blade,
said slide member:
  slidably received in said housing, and
  having at one of its ends a handle portion which extends outside said housing, and
  having said blade attached to it at its other end,
said housing:
  having means to slidably receive said slide member, and
  having an aperture to guide a tube to be severed into the path of said blade, and
  having an aperture in a sidewall to receive said handle portion of said slide member, and
  having abutting means to abut a portion of said slide member to prevent sliding removal of said slide member through said sidewall, and
  having means to receive said resilient biasing means,
said resilient biasing means disposed in said housing to bias said slide member against said abutting means,
characterized by the direction of sliding travel of said slide member being normal to the axis of said tube to be severed and by said blade:
  being a portion of a razor blade and being V-ground, and
  being attached to said slide member with its cutting edge at an angle to the direction of travel of said slide member, and
  being attached to said slide member with its unground surfaces at an angle to the upper sliding surface of said slide member, and
  being attached to said slide member with its unground surfaces at an angle to a plane transverse to the direction of travel of said sliding member, and
  being attached at such angles that the plane of one of said V-ground surfaces is parallel to the direction of sliding travel of said slide member and normal to the axis of said tube to be severed.

7. In a device for transversely severing a polymeric synthetic resinous artificial insemination tube,
a housing,
an elongated slide member having two ends,
resilient means to bias said slide member, and
a cutting blade,
said slide member:
  slidably received in said housing, and
  having at one of its ends a handle portion which extends outside said housing, and
  having said blade attached to it at its other end,
said housing:
  having means to slidably receive said slide member, and
  having an aperture to guide a tube to be severed into the path of said blade, and
  having an aperture in a sidewall to receive said handle portion of said slide member, and
  having abutting means to abut a portion of said slide member to prevent sliding removal of said slide member through said sidewall, and
  having means to receive said resilient biasing means,
said resilient biasing means disposed in said housing to bias said slide member against said abutting means, characterized by the direction of sliding travel of said slide member being normal to the axis of said tube to be severed and by said blade:
being a portion of a razor blade and being V-ground, and
being attached to said slide member at an angle to each of three directions,
the first of said directions being the direction of sliding travel of said slide member,
the second of said directions being the direction which is normal to said direction of travel and parallel to the axis of the tube to be severed,
the third of said directions being the direction which is normal to both said first and said second directions, and
being attached at such angles that the plane of one of said V-ground surfaces is parallel to the direction of sliding travel of said slide member and normal to the axis of said tube to be severed.

* * * * *

UNITED STATES PATENT AND TRADEMARK OFFICE
CERTIFICATE OF CORRECTION

PATENT NO. : 4,000,561
DATED : January 4, 1977
INVENTOR(S) : Horst K. Wieder and Klaus A. Wieder It is certified that error appears in the above-identified patent and that said Letters Patent are hereby corrected as shown below:

Column 2, lines 6 and 7, change "comprising on cams" to -- comprising no cams --; Column 3, line 61, change "in a straw 30"; to -- in straw 30 --; Column 9, line 20, change "having to slidably receive" to -- having means to slidably receive --.

Signed and Sealed this second Day of August 1977

[SEAL]

Attest:

RUTH C. MASON
*Attesting Officer*

C. MARSHALL DANN
*Commissioner of Patents and Trademarks*